US006162205A

United States Patent [19]

Shichi et al.

[11] Patent Number: 6,162,205

[45] Date of Patent: Dec. 19, 2000

[54] CONTAINER FOR THERAPEUTIC USE

[75] Inventors: Hiroyuki Shichi, Tokyo; Takao Yoshida, Saitama; Tatsuo Suzuki, Tokyo; Keinosuke Isono, Saitama, all of Japan

[73] Assignee: Mateial Engineering Technology Laboratory, Incorporated, Tokyo, Japan

[21] Appl. No.: 09/176,568

[22] Filed: Oct. 21, 1998

[30] Foreign Application Priority Data

Nov. 4, 1997 [JP] Japan .................................... 9-316609

[51] Int. Cl.[7] .................................................... A61B 19/00

[52] U.S. Cl. .......................... 604/416; 604/410; 604/408; 206/204; 206/205; 206/219

[58] Field of Search ..................................... 604/403–416; 206/204, 205, 219

[56] References Cited

U.S. PATENT DOCUMENTS 5,267,646 12/1993 Inoue et al. ............................. 206/204
5,423,421 6/1995 Inoue et al. ............................. 206/219

*Primary Examiner*—Glenn K. Dawson
*Assistant Examiner*—William Noggle
*Attorney, Agent, or Firm*—Knobbe, Martens, Olson & Bear, LLP

[57] ABSTRACT

A container for therapeutic use is formed of a main body, which is made of a flexible resin and provided with a bag portion. The bag portion is formed in a flat shape at at least a part thereof where mutually-opposing walls of the bag portion are peelably welded together at inner surfaces thereof to form a welded region. A hole is formed as an attachment hole through at least one of the mutually-opposing walls in the welded region. A holder with a medicament placed therein, said medicament being prone to a change in property or color upon absorption of moisture, is hermetically attached to the at least one wall over the attachment hole to seal the medicament in the holder. A moisture-barrier member with a desiccant placed therein is arranged on a side opposite to the holder so that the other wall of the bag portion is hermetically covered by the moisture-barrier member at a position at least corresponding to the attachment hole.

14 Claims, 9 Drawing Sheets

CONTAINER FOR THERAPEUTIC USE

BACKGROUND OF THE INVENTION a) Field of the Invention

This invention relates to a container for therapeutic use, and more specifically to a container for therapeutic use, which contains a base solution and a medicament, which is susceptible to a change in property or color by moisture, oxygen and/or the like, in different compartments for stable storage over an extended time. Especially, the present invention is concerned with a container for therapeutic use, which allows a desiccant to retain its dehumidifying function over a long time so that the interior of a compartment with a medicament placed therein can be fully maintained under dry conditions.

b) Description of the Related Art

Containers for therapeutic use, each of which generally has a structure such that two or more medicinal ingredients are separately held during storage and upon use, are aseptically combined together for administration, have already been proposed (JP kokai 63-19149, JP kokai 1-240469 and JP kokai 2-4671). These containers are intravenous hyperalimentation (IVH) containers. Mutually-opposing walls of a bag-portion of each container are thermally and peelably welded and sealed together in a lateral direction to divide the interior of the container into two compartments. A sugar solution is stored in one of the compartments, while an amino acid solution is stored in the other compartment. As the sugar solution and the amino acid solution are kept separated from each other during storage in such an infusion fluid container, the sugar and the amino acid as medicinal ingredients are prevented from reacting with each other and undergoing changes in properties in the course of autoclave sterilization treatment or during storage. Upon use, peeling of the peelable seal, which divides the above-mentioned two compartments from each other, by an operation from the outside makes it possible to aseptically combine the respective medicinal ingredients together with ease.

Other dual-compartment containers have also been proposed, in each of which a lyophilized product such as an antibiotic or a protein preparation is held in one of the compartments and a dissolving solution for the protein preparation is held in the other compartment (JP kokai 4-364850, JP kokai 4-364851, JP kokai 6-14975). Since a lyophilized product such as an antibiotic is apt to be easily deteriorated by moisture or oxygen, only the accommodative compartment for the dry medicament is covered by a covering material having moisture or gas barrier properties.

Incidentally, an attempt for the provision of a covering material equipped with complete barrier property results in one carrying thereon a deposited layer or thin film layer of aluminum. As such a covering material permits practically no permeation of external moisture or oxygen, the covering material can exhibit its function over an extended time without requiring a desiccant or deoxidizer in a large amount.

However, such a covering material lacks transparency. For a container for therapeutic use, it is required before use to permit confirming that each medicinal ingredient contained therein is free of abnormality. Accordingly the covering material is also required to have transparency. When a barrier film having transparency and resistance to moisture or gas permeation is used in a container for therapeutic use, a desiccant or deoxidizer inside the container is desired to retain its function for 3 years or longer.

A lyophilized product is aseptically transferred to and filled in an accommodative compartment of a container for therapeutic use after conducting lyophilization in a separate vessel. This filling operation may be cumbersome.

SUMMARY OF THE INVENTION

An object of the present invention is therefore to provide a container for therapeutic use, which permits easy aseptic filling and also maintenance of the function of a desiccant, which serves to protect a medicament from a change in property, over a long time.

In a first aspect of the present invention, there is thus provided a container for therapeutic use, said container being formed of a main body made of a flexible resin and provided with a bag portion, said bag portion being formed in a flat shape at at least a part thereof where mutually-opposing walls of the bag portion are peelably welded together at inner surfaces thereof to form a welded region, wherein:

- a hole is formed as an attachment hole through at least one of the mutually-opposing walls in the welded region;
- a holder with a medicament placed therein, said medicament being prone to a change in property or color upon absorption of moisture, is hermetically attached to the at least one wall over the attachment hole to seal the medicament in the holder;
- a moisture-barrier member with a desiccant placed therein is arranged on a side opposite to the holder so that the other wall of the bag portion is hermetically covered by the moisture-barrier member at a position at least corresponding to the attachment hole.

Preferably, the holder has a wall the moisture permeability [P1] of which falls within a range not higher than 1/10 of a permeability [P2] of the other wall of the bag portion at the position corresponding to the attachment hole. The permeability [P1] of the wall of the holder may preferably be not higher than 1.0 $g/m^2 \cdot day$ as measured at 40° C. and 0–90% R.H. difference. The wall of the holder may preferably be provided with a cyclic olefin resin layer. Desirably, a through-hole may be formed through both the walls of the bag portion in the joined region, an opening formed in the one wall of the bag portion by the through-hole acts as the attachment hole, and an opening formed in the other wall of the bag portion by the through-hole may be hermetically covered by a cover member having a permeability [P2] of at least 4.00 $g/m^2 \cdot day$ as measured at 40° C. and 0–90% R.H. difference so that the cover member may act as the other wall of the bag portion at the position corresponding to the cover member. The cover member may preferably be made of a silicone rubber sheet. Preferably, the cover member may be made of a microporous film moisture free permeability, which may have a particle blocking rate of at least 99% for particles having diameters of at least 0.8 $\mu m$ and a water impermeability of at least 500 $mmH_2O$ in terms of water pressure resistance. Desirably, the medicament may be a lyophylized product subjected to lyophilization within the holder.

More desirably, the holder has a wall the moisture permeability [P1] of which falls within a range of from 1/10 to 1/1000 of a permeability [P2] of the other wall of the bag portion at the position corresponding to the attachment hole.

In a second aspect of the present invention, there is also provided a process for the production of a container for therapeutic use as defined above as the first aspect, which comprises:

- thermally and peelably welding mutually-opposing walls of a bag portion of a flexible container together at inner surfaces thereof to form a welded region at at least a part of the bag portion;

forming a through-hole in both the walls of the bag portion in the welded region;

attaching a holder with a medicament placed therein, said medicament being prone to a change in property or color upon absorption of moisture, onto one of the walls so that an opening formed as on attachment hole in the one wall by the through-hole is covered by the holder;

covering an opening, which has been formed in the other wall by the through-hole, by a cover member having a moisture permeability of at least 4.00 g/m$^2$·day as measured at 40° C. and 0–90% R.H. difference; and attaching a moisture-barrier member, which contains a desiccant placed therein, onto the other wall of the bag portion on a side opposite to the holder so that the cover member is hermetically covered by the moisture-barrier member.

In the container for therapeutic use having the construction as described above, the medicament is filled and lyophilized in the holder and, while being kept under aseptic conditions, the holder with the medicament held therein is attached to the joined region of the main body of the container. Upon production of the container, aseptic operation can be achieved simply and easily. Further, the other wall of the bag portion or the cover member as a substitute for the other wall of the bag portion is hermetically covered by the moisture-barrier member at the position corresponding to the attachment hole. On the side opposite to the holder and at the position corresponding to the attachment hole, the desiccant is arranged with the other wall of the bag portion or the cover member interposed between the desiccant and the holder, so that the desiccant absorbs moisture entered permeating through the other wall of the bag portion or the cover member. The desiccant is hermetically covered by the moisture-barrier member, thereby preventing the desiccant from absorbing moisture in the surrounding atmosphere. A space formed between the other wall of the bag portion or the cover member and the moisture-barrier member acts as a drying area for the interior of the holder. The desiccant can retain its function for a long time because it absorbs only moisture entered permeating through the wall of the holder and further through the other wall of the bag portion or the cover member and absorbs practically no moisture from the surrounding atmosphere.

DETAILED DESCRIPTION OF THE INVENTION

Figure 1:
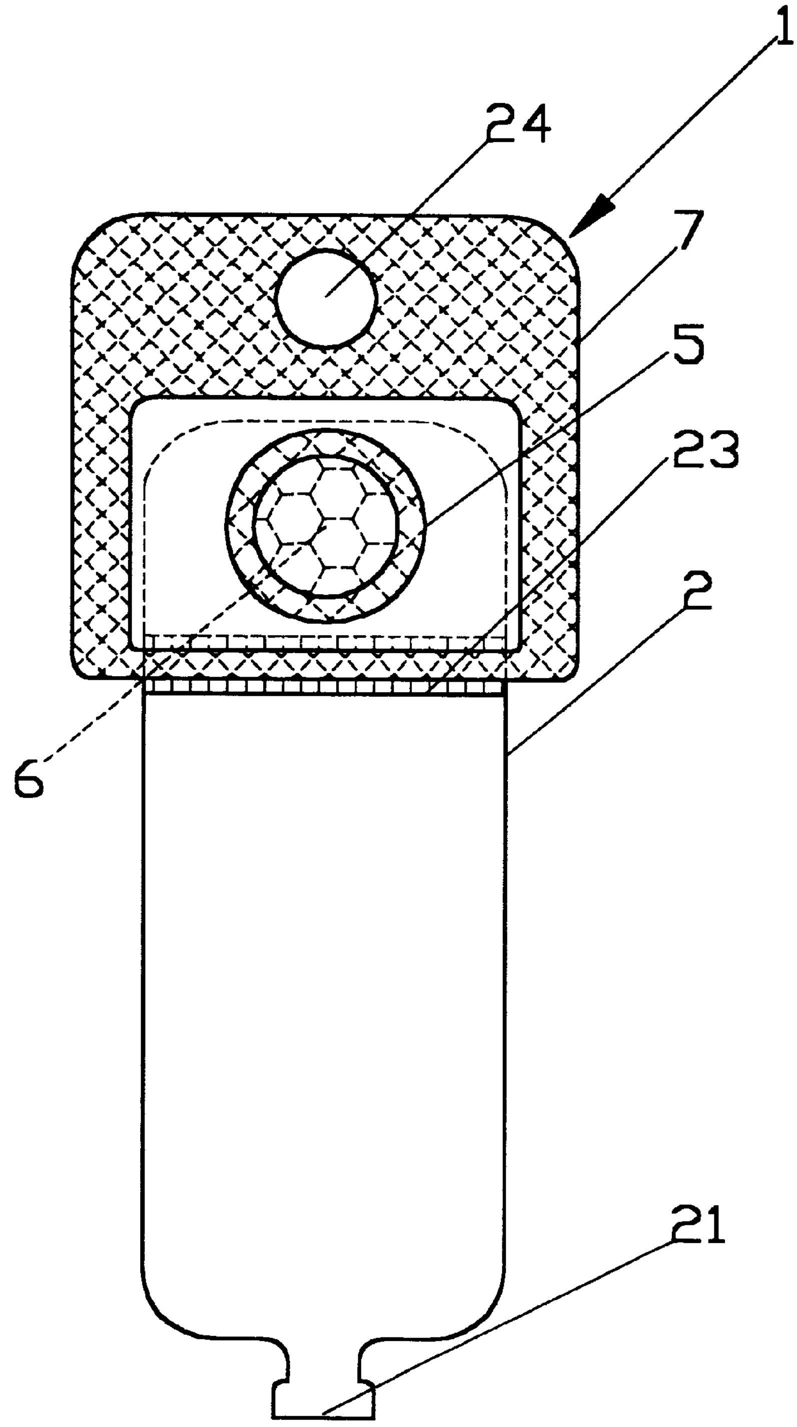
FIG. 1 is a plan view of a container for therapeutic use according to a first embodiment of the present invention.

The container main body made of the flexible resin is a non-fixed volume container having at least a flexible wall. The bag-portion of the main body is formed in a flat shape which is composed of two walls arranged opposing each other. The main body has been formed from a film, tube or sheet obtained by blown film extrusion, or has been formed by extrusion, injection molding or blow molding.

Examples of the resin material for the container for the therapeutic use can include general-purpose resins such as polyolefin resins, vinyl chloride resin, vinylidene chloride resins, polyester resins, polyvinyl alcohol resins, polyacrylonitrile resins, polyacrylic acid resins, and polyamide resins. The resin-made container may be formed of a single layer or multiple layers. The innermost layer, which is brought into contact or remains in contact with the medicament in the container, may desirably be formed of a resin which does not affect the medicament or does not produce an eluted matter. As such a resin, a polyolefin resin is desired. Illustrative of the polyolefin resin are lower olefin resins such as low-, medium- or high-density polyethylene and polypropylene, cyclic polyolefins, and copolymers of two or more of lower olefins and/or cyclic olefins.

In the bag portion, the joined region is formed by peelably joining the two walls together at the inner surfaces thereof. The hole is formed in the joined region by a punch or the like, so that the attachment hole is formed.

The joined region can be a liquid-tight seal formed with an adhesive, a thermally-welded seal, or the like. Illustrative of the adhesive for the seal are solvent-type adhesives such as ketone-type solvents, ester-type solvents, ether-type solvents, hydrocarbon-type solvents and halogenated-hydrocarbon-type solvents; and resin-base adhesives such as modified olefins and hot melts. On the other hand, illustrative of the thermally-welded seal are seals welded by external heating such as heat sealing or impulse sealing; and seals welded by internal heating such as ultrasonic welding or high-frequency welding.

The joined region is a peelably-sealed region. The peelably-sealed region is generally called a "peelable seal" region or a "weak seal" region, which is a seal region peelable when the compartment or container is pressed from the outside and its interior is brought into a state pressurized to a predetermined level or which is a seal region peelable when the two walls of the bag-portion are held by hands and are pulled in directions away from each other. The peel strength of the peelable seal region may desirably be of such a level that the peelable seal region is peeled off when the internal pressure of the compartment is raised to 0.01 to 1.0 Kgf/cm$^2$, especially 0.05 to 0.5 Kgf/cm$^2$. Peel strength lower than the above range cannot provide safety sufficient to maintain the medicament and, for example, its dissolving solution under conditions isolated from each other during production, shipping, storage and the like. On the other hand, peel strength higher than the above range may lead to a potential problem in that communicating operation may not be readily performed upon use.

When the peelable joined region is formed by thermal welding, the innermost layer of the container main body may desirably be formed of a resin blend. Particularly desired is a blend of resins which are different in thermal fusion initiating temperature or Vicat softening point and are not very compatible with each other. Provision of a layer of such a resin blend makes it possible to easily set a suitable sealing temperature for the peelably-welded seal. This also makes it possible to precisely set the seal strength required for the peelably-welded seal, namely, the balancing between the peelability by external force upon use and the seal strength preventing peeling during storage. When resins which are not very compatible with each other are molten and blended together and the resulting blend is formed into a sheet as an inner layer, the inner layer, at a surface thereof, is divided on the order of micrometers into areas having different thermal weldability. By controlling the thermal fusion properties of the individual areas of the micrometer order in the surface of the sheet at a given temperature, the degree of the seal strength can be precisely determined and the above-described advantageous effect can be easily brought about.

In the present invention, two or more joined regions may be arranged to separately store three or more medicinal ingredients. Further, the container main body may be provided with one or more. peelably-joined narrow seals which divide the interior of the main body into two or more sections. In this case, the peelably-joined narrow seals may serve as joined regions.

As has been described above, the attachment hole is formed in the joined region. The attachment hole is formed by forming a hole in at least one of the two walls of the bag portion. For the convenience of production, however, it is desired to form the hole through both of the walls. When the hole is formed through both of the walls, an opening in one of the walls serves as the attachment hole, and the cover member is arranged over an opening in the other wall.

The holder is hermetically attached over the attachment hole. The holder is generally formed of a cup-shaped, molded resin product, and a flange is generally formed around its opening. The flange is fixed on a peripheral edge of the attachment hole. Although the flange may be hermetically fixed with an adhesive, it is desirable to hermetically fix the flange by thermal welding. Because, the adhesive has a potential problem in that it may deleteriously affect the medicament stored in the holder. The medicament which is hermetically stored within the holder is hygroscopic and tends to change in property or color upon absorption of moisture. In the present invention, the holder may desirably be a molded product of a transparent resin with a fixing flange portion formed around its opening. More desirably, the resin may be resistant to the permeation of moisture.

With the foregoing in view, the holder may desirably be made of a thermoplastic resin material which allows to readily mold or otherwise form the flange and the like, with a transparent thermoplastic resin material carrying no aluminum layer or the like thereon being more desired. Further, the material of the holder may desirably a resin material which does not adversely affect the medicament and has low moisture permeability.

Desired examples of such a resin material can include polyolefin resins, for example, lower olefin resins such as low-, medium- or high-density polyethylene and polypropylene, cyclic polyolefins, and copolymers of two or more of lower olefins and/or cyclic olefins. To impart moistureproofness to the resin material, it is desired to provide the resin material with a layer of a cyclic polyolefin or a copolymer of a cyclic olefin monomer with another olefin monomer or with a deposited silica layer.

In the present invention, the joined region is hermetically covered by the moisture-barrier member, and the desiccant is arranged inside the member.

The moisture-barrier member may be a sheet which is provided with a layer of aluminum or the like and does not permit permeation of moisture, a low-permeability sheet which permits only extremely slight permeation of moisture, or a shaped product of such a sheet. To assure the desiccant to retain its function, the sheet may desirably be an impermeable sheet provided with a layer of aluminum or the like so that moisture is not allowed to permeate substantially.

Described specifically, such a moisture-barrier member is provided with a metal layer or deposited layer of aluminum or the like; a layer of a resin having high barrier property to moisture, such as polyvinylidene chloride, polytetrafluoroethylene, polyethylene trifluoride, rubber hydrochloride, polyethylene or polypropylene; or a deposited layer of an earth metal or metal such as aluminum, silicon, magnesium, titanium, silver or gold, or of an oxide thereof. These layers are substantially or completely impervious to gas.

The desiccant arranged inside the moisture-barrier member is a substance having strong hygroscopicity by itself, and can be a chemical desiccant or a physical desiccant. Preferred examples of the desiccant can include silica gel, activated alumina, calcium chloride, and molecular sieves. From the standpoint of the capacity of the desiccant, one capable of lowering the remaining water content to $5\times10^{-3}$ mg or less in 1 l of air is desired. Such a desiccant can lower the absolute humidity to the above-described range, thereby making it possible to promptly absorb moisture in the holder.

The medicament is aseptically filled in the holder. The medicament can be in the form of a dry solid such as powder, a mass or granules or in some rare instances, in the form of a solution. Described specifically, the medicament can be an antibiotic, physiologically-active substance, hormone, vitamin or synthetic medicament, which has been filled in the holder by in situ lyophilization. Incidentally, examples of the medicament can also include oxygen-susceptible medicaments which are readily changed in property by oxygen. For such medicaments, a deoxidizer or the like is therefore needed.

A solution is stored in the main body of the container. The solution may be simple aseptic water for dissolution or a infusion solution containing an electrolyte, sugar, amino acids, vitamins and the like. From the standpoint of safety, it is desired to hermetically fill such a solution in the main body and generally, to subject the solution to autoclave sterilization treatment. This autoclave sterilization treatment is conducted at 100° C. to 140° C.

A description will next be made in short about one example of a process for the production of the container for therapeutic use according to the present invention. First, a flat container main body is formed, and a peelable joined region is then formed in a bag portion at a predetermined position. A solution is next filled and sealed in the main body, and is subjected to autoclave sterilization treatment. Either before or after the sterilization, an attachment hole is formed in the joined region. The above-described holder with a medicament aseptically held therein is hermetically connected to the container main body. This connection is conducted in a clean and aseptic atmosphere. Subsequent to the connection, the joined region is hermetically covered by a moisture-barrier member. Upon covering by the member, a desiccant is inserted inside the member.

In the container of therapeutic use according to the present invention, the holder may preferably has a wall the moisture permeability of which falls within a range not greater than 1/10 of a permeability of the other wall of the bag portion at the position corresponding to the attachment hole.

Figure 2:
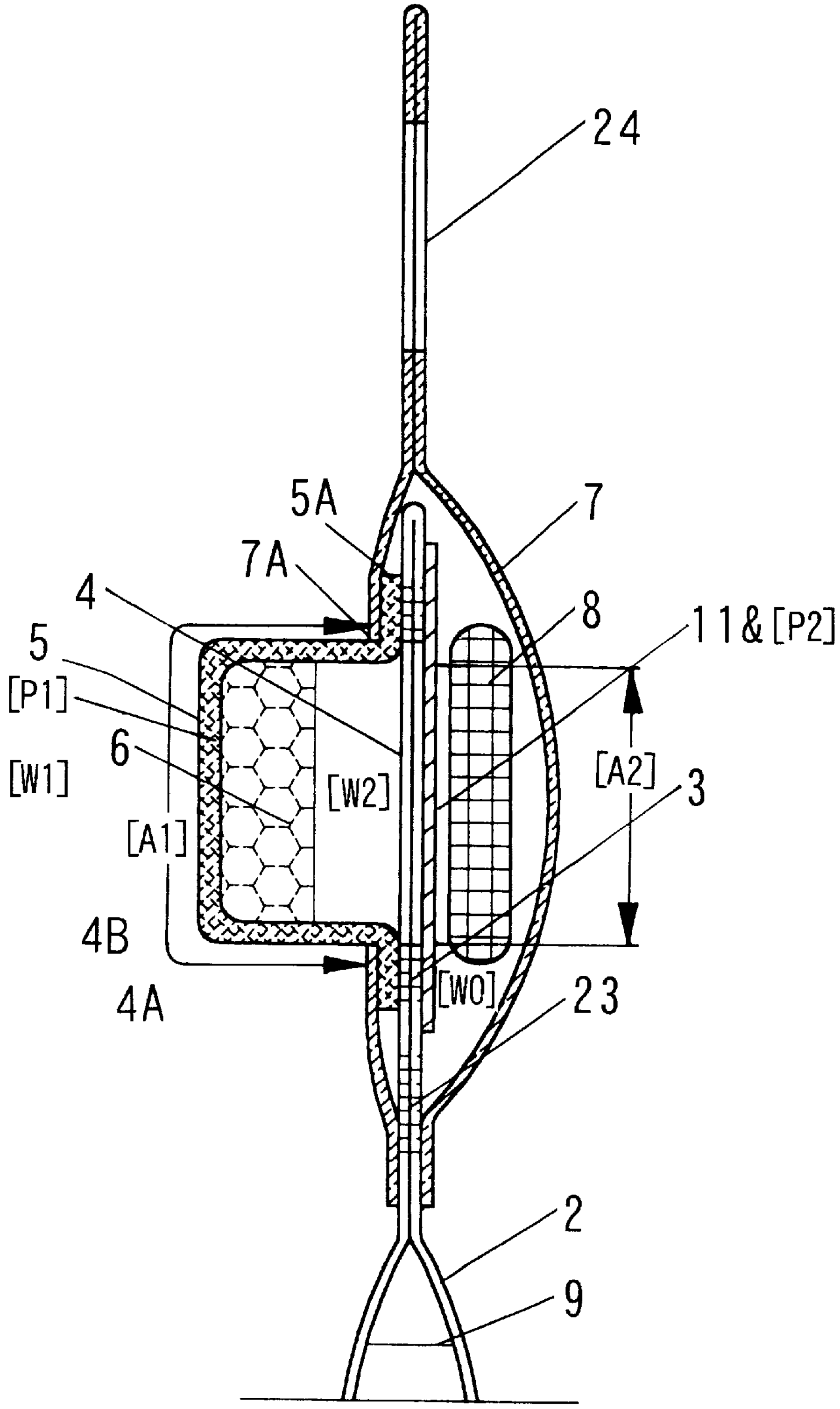
FIG. 2 is a fragmentary side cross-sectional view of the container for therapeutic use according to the first embodiment.

The wall of the bag portion, said wall being a wall located opposite the position of the attachment hole in the container for therapeutic use according to the present invention, may be the wall itself of the bag portion. As is illustrated in FIG. 2, a thorough-hole may be formed through both the walls of the bag portion, whereby an opening is formed as the attachment hole in the one wall and another opening is also formed in the other wall at the same time. In this case, the cover member may serve as the other wall of the bag portion. Desirably, the ratio [P2]/[P1] of the moisture permeability [P2] of the other wall of the bag portion or the cover member to the moisture permeability [P1] of the wall of the holder may fall within the range not greater than 1/10, especially within the range not greater than 1/50.

Now assume, for example, that the moisture permeability of each wall of the holder is [P1] and the moisture permeability of the other wall of the bag portion or the cover member is [P2]. Let's also assume that the water vapor pressure outside the holder is [W1] and the water vapor pressure inside the holder is [W2]. Also assume that the water vapor pressure of the interior of the moisture-barrier member, said interior being isolated from the interior of the holder with the other wall of the bag portion or the cover member interposed therebetween, is [W0]. Owing to the arrangement of the desiccant, [W0] is practically very close to 0. Also assume that the area of the wall of the holder is [A1] and the other wall of the bag portion or the cover member at the position corresponding to the attachment hole is [A2]. Further assume that the permeation rate of moisture from the surrounding atmosphere into the holder is dM/dt and the permeation rate of moisture from the holder is dm/dt. The following equations can then be derived.

$$dM/dt=[A1]\cdot[P1]([W1]-[W2])$$

$$dm/dt=[A2]\cdot[P2]([W2]-[W0])$$

When the function of the desiccant is exhibited and an equilibrium is reached, the following relation is established: dM/dt=dm/dt. Accordingly, the following equation can be derived:

$$[A1]\cdot[P1]([W1]-[W2])=[A2]\cdot[P2]([W2]-[W0])$$

Here, the water vapor pressure [W0] inside the moisture-barrier member, where the desiccant is disposed, is lowered close to 0. As a consequence, the following equation can be obtained:

$$[A1]\cdot[P1]([W1]-[W2])=[A2]\cdot[P2]\cdot[W2]$$

By rewriting this equation, the following equation can be derived.

$$[W2]=[A1]\cdot[P1]\cdot[W1]/([A1]\cdot[P1]+[A2]\cdot[P2])$$

When the wall area ratio [A1]/[A2] is 2/1 and the moisture permeability ratio [P1]/[P2] is 1/10, [W2]=[W1]/6 is obtained. Assuming that the water vapor pressure [W1] of the surrounding atmosphere is 21.4 mmHg, the water vapor pressure inside the holder is calculated to be 3.57 mmHg.

Accordingly, setting of the moisture permeability ratio of the wall of the holder to the other wall of the bag portion or the cover member within the above-described range makes it possible to dry the interior of the holder to such an extent as satisfactorily inhibiting the absorption of moisture in the medicament.

The moisture permeability [P1] of the wall of the holder may be desirably 1.0 $g/m^2\cdot day$ or lower (as measured at 40° C. and 0–90% R.H. difference), more desirably 0.5 $g/m^2\cdot day$ or lower (as measured at 40° C. and 0–90% R.H. difference), notably 0.05 $g/m^2\cdot day$ or lower (as measured at 40° C. and 0–90% R.H. difference).

If the moisture permeability of the wall of the holder is lower than the upper limit described above, the total amount of moisture which may enter the holder from the surrounding atmosphere can be controlled small so that the desiccant can retain its function over a long time. Further, the moisture permeability ratio of the wall of the holder to the other wall of the bag portion or the cover member can be easily set at a desired value.

Preferably, the wall of the holder may be provided with a layer of a cyclic olefin resin.

The arrangement of the layer of the cyclic olefin resin on the wall of the holder makes it possible to easily control the moisture permeability of the wall of the holder at the above-described upper limit or lower. As the resin, one having safety to the medicament and sufficient transparency is preferred.

Illustrative of the cyclic olefin resin are thermoplastic norbornene resins already known to the public (as disclosed in JP kokai 5-317411), for example, homopolymers of 2-norbornene, 5-methyl-2-norbornene, 5,5-dimethyl-2-norbornene, 5-ethyl-2-norbornene, 5-ethylidene-2-norbornene and 5-butyl-2-norbornene. The cyclic olefin resin may be a copolymer of a cyclic olefin and another olefin. Examples of such a copolymer can include random copolymers of cyclic olefins and ethylene already known to the public (as disclosed in JP kokai 8-155007) and their hydrogenated products.

In the above-described container for therapeutic use, a through-hole may be formed in the joined region, an opening formed in the one wall of the bag portion as a result of the formation of the through-hole may be used as the above-described attachment hole, and an opening in the other wall may be hermetically covered by a cover member having a moisture permeability of 4.00 $g/m^2\cdot day$ or higher (as measured at 40° C. and 0–90% R.H. difference), especially of 20.0 $g/m^2\cdot day$ or higher (as measured at 40° C. and 0–90% R.H. difference).

For the formation of the attachment hole in the one wall of the bag portion, it is an extremely simple method from the standpoint of production to form the through-hole in the joined region.

When a hole is formed in only one of the walls rather than forming it as a through-hole through both the walls, the other wall at a position corresponding to the attachment hole is left, as is, so that the interior of the holder and that of the moisture-barrier member are partitioned from each other.

When a through-hole formed at the joined region, however, the cover member acts as the other wall located at the position corresponding to the attachment hole. If the cover member is pervious to moisture, the above-mentioned ratio of the permeability [P1] of the wall of the holder to the permeability [P2] of the other wall of the bag portion the position corresponding to the attachment hole can be easily achieved.

Desirably, the cover member may be formed of a silicone rubber sheet.

The silicone rubber sheet contains a rubber or elastomer and has sufficient moisture permeability. It also has high safety for use in therapy. If the silicone rubber sheet has a thickness in a range of from 20 to 2,000 μm, for example, its moisture permeability may range from 50 to 2,000 $g/m^2 \cdot day$ (as measured at 40° C. and 0–90% R.H. difference). When such a sheet is employed as the above-mentioned cover member, moisture which may have entered the holder in the course of production of the container for therapeutic use can be promptly eliminated by allowing it to permeate out through the cover member.

The cover member may preferably be made of a microporous film of moisture free permeation, which has a particle blocking rate of at least 99% for particles having diameters of at least 0.8 μm and a water impermeability of at least 500 $mmH_2O$ in terms of water pressure resistance.

It is not necessary for the microporous film to make up the whole cover member. It is sufficient if at least a part of the cover member is made of the microporous film. When such a microporous film is used as the cover member, that is, as the other wall of the bag portion at the position corresponding to the attachment hole, the interior of the holder can be maintained in the same dry state as the space with the desiccant contained therein because the microporous film permits substantially free permeation of moisture or the like therethrough. As a consequence, the medicament can be stably stored even if it is hygroscopic.

Examples of the microporous film can include a microporous film formed by flash-spinning a general-purpose thermoplastic resin such as polypropylene or polyethylene and putting the resultant fibers together under heat and pressure; a microporous film obtained by mixing fine particles of silica, talc, calcium carbonate or the like or fine oil droplets with polyethylene, polypropylene or the like, forming the resultant mass into a film, optionally stretching the thus-formed film, and then removing the fine particles or fine oil droplets; and microporous sheets formed by thermally cohering fine particles of a thermoplastic resin together.

The cover member made of such a microporous film permits ready permeation of moisture, gas and the like owing to the existence of micropores. The particle blocking rate may desirably be 99% or higher when the particle diameter is 0.8 μm or greater, preferably 0.6 μm or greater, more preferably 0.4 μm or greater. A microporous film having such a particle blocking rate permits practically no passage of bacteria or the like. In particular, a microporous film the particle blocking rate of which is 99% or higher at a particle diameter of 0.4 μm or greater can fully inhibit passage of disrupted proteinaceous fragments of bacteria or the like.

The microporous film may desirably be a water-impervious, microporous film the water pressure resistance of which is 500 $mmH_2O$ or higher, preferably $1\times10^3$ $mmH_2O$, more preferably $8\times10^3$ $mmH_2O$. When the joined region is peeled off upon use and the resulting solution in the container is brought into contact with the cover member, the microporous film with water pressure resistance in the above range is free of the potential danger that the resulting solution may leak out through the cover member or, even if such leakage takes place, the cover member is free of the potential danger that the leaked solution may return in to the container. Water pressure resistance lower than the above range, on the other hand, leads to a greater potential danger that the resulting solution may leak out through the cover member. Such water pressure resistance may be exhibited by the material itself of the microporous film or may be imparted by treating the microporous film with a water-repellant chemical substance.

In the container for therapeutic use, the medicament may preferably be in the form of a lyophilized product subjected to lyophilization within the holder.

Lyophilization may usually be conducted in a vial equipped with a mouth which is either completely closable or semi-closable by a rubber stopper. If the holder can perform the role of the vial, it is possible to obviate an operation which would otherwise be required to transfer the hygroscopic medicament from the vial into the holder. This makes it possible to minimize the potential problems of contamination and moisture absorption of the medicament from the surrounding atmosphere, which may take place upon incorporating the medicament in the container for therapeutic use.

Preferred embodiments of the container for therapeutic use according to the present invention will hereinafter be described in detail with reference to the accompanying drawings.

First Embodiment

As is illustrated in FIG. 1 and FIG. 2, a container 1 for therapeutic use according to the first embodiment of the present invention is formed of a main body made of a flexible resin. Either a part or the entire part of a bag portion 2 of the main body is the bag portion 2 are thermally and peelably welded together at inner surfaces thereof, whereby a welded region 3 is formed. At the welded region 3, an opening 4A is formed as an attachment hole 4 through one of the walls. Extending over the attachment hole 4, a transparent holder 5 is thermally welded in an air- and liquid-tight fashion on the one wall. Accommodated inside the holder 5 is a lyophilized medicament 6, which tends to absorb moisture and to undergo a change in property or color. At a position corresponding to the attachment hole 4, another opening 4B is formed through the other wall of the bag portion 2. On a side opposite to the holder 5, a cover member 11 is thermally welded and fixed in an air- and liquid-tight fashion on the other wall so that the opening 4B is closed. This cover member 11 is hermetically covered by a moisture-barrier sheet 7, and a desiccant 8 is placed inside the sheet 7.

Describing in further detail the container 1 for therapeutic use according to the first embodiment, each wall of the bag portion 2 of the container 1 for therapeutic use has a thickness of 200 μm. In its flattened form, the bag portion 2 is 150 mm in length and 80 mm in width. The capacity of the bag portion 2 is 160 ml. Each wall of the bag portion 2 is formed of two layers, that is, an outer layer and an inner layer. The outer layer is 150 μm in thickness and is made of linear low-density polyethylene (density: 0.935 $g/cm^3$, MI: 2, melting point: 121° C.), while the inner layer is 50 μm in thickness and is made of a 2:1 resin blend of linear low-density polyethylene (density: 0.935 $g/cm^3$, melting point: 121° C.) and polypropylene (density: 0.900 $g/cm^3$, MI: 0.7, melting point: 165° C.).

The container 1 for therapeutic use is provided with a discharge port 21, which is hermetically closed by a rubber stopper after the container 1 is filled with a dissolving solution 9. A peelable, welded narrow seal portion 23 is laterally formed in the bag portion 2 so that the narrow seal portion 23 divides the interior of the bag portion 2 into two compartments. The narrow seal portion 23 and the welded region 3 have been formed to have such seal strength as they are peeled off when the internal pressure of the bag portion 2 is raised to 0.2 $Kgf/cm^2$.

The holder 5 is arranged over the attachment hole 4. The holder 5 has been formed by vacuum forming a transparent thermoplastic resin sheet. The holder 5 has been formed in the shape of a cup, and is provided with a flange portion 5A around an opening thereof. The flange portion 5A and a peripheral edge portion of the attachment hole 4 have been thermally welded and sealed together in an air- and liquid-tight fashion, whereby the holder 5 is attached to the outer surface of the one wall of the bag portion 2 by way of the flange portion 5A. The holder 5 has been formed from a resin sheet composed of an outer layer, a middle layer and an inner layer. The outer layer is 100 $\mu$m in thickness and is made of low-density polyethylene. The middle layer is 2,000 $\mu$m in thickness and is made of a cyclic polyolefin ("APL 6013", trade name; product of Mitsui Petrochemical Industries, Ltd.). The inner layer is 100 $\mu$m in thickness and is made of linear low-density polyethylene. The moisture permeability [P1] of the wall of the holder 5 is 0.03 to 0.05 $g/m^2 \cdot 24$ hr (as measured at 40° C. and 0–90% R.H. difference).

The cover member 11 is formed of a linear low-density polyethylene sheet of 100 $\mu$m in thickness. The moisture permeability [P2] of the cover member 11 is 4.90 to 5.00 $g/m^2 \cdot hr$ (as measured at 40° C. and 0–90% R.H. difference).

An upper part of the bag portion 2 is covered in a liquid-tight fashion by the humidity-barrier sheet 7. The upper part extends from an end portion, which is located on a side opposite to the discharge port 21, to a portion located somewhat the way down beyond the narrow seal portion 23. The sheet 7 is folded with the upper part of the bag portion 2 held between the thus-folded two parts of the sheet 7, and is thermally welded on outer surfaces of the walls of the barrel portion at the narrow seal portion 23. Further, the folded two parts of the sheet 7 are thermally welded and sealed together at side peripheral edges and upper portions thereof. A hole is formed as a hang-up hole 24 through the thermally welded and sealed upper portions. Further, an opening 7A is formed in the sheet 7 at a predetermined position so that holder 5 extends through the opening 7A. A peripheral edge portion of the opening 7A and an outer surface of the flange portion 5A of the holder 5 are thermally welded and sealed together. Accordingly, the upper part of the bag portion 2 is hermetically covered by the sheet 7 except for a portion corresponding to the holder 5. Between the sheet 7 and the cover member 11, the desiccant 8 is arranged.

The sheet 7 is a laminated film, which is provided with an aluminum layer as a middle layer and also with a sealant layer, i.e., a low-density polyethylene layer as an innermost layer. As the desiccant 8, a molecular sieve is contained in an amount: as much as 6 grams. The desiccant 8 has drying ability sufficient to reduce the amount of moisture, which remains in 1 l of air, to $3 \times 10^{-3}$ mg or further.

The dissolving solution 9 is hermetically stored in the main body of the container 1. Together with the main body of the container 1, the dissolving solution 9 has been subjected to autoclave sterilization treatment. The medicament (lyophilized product) 6 is aseptically filled and stored in a dry state within the holder 5.

A description will next be made in brief about a process for the production of the container 1 for therapeutic use.

Figure 3:
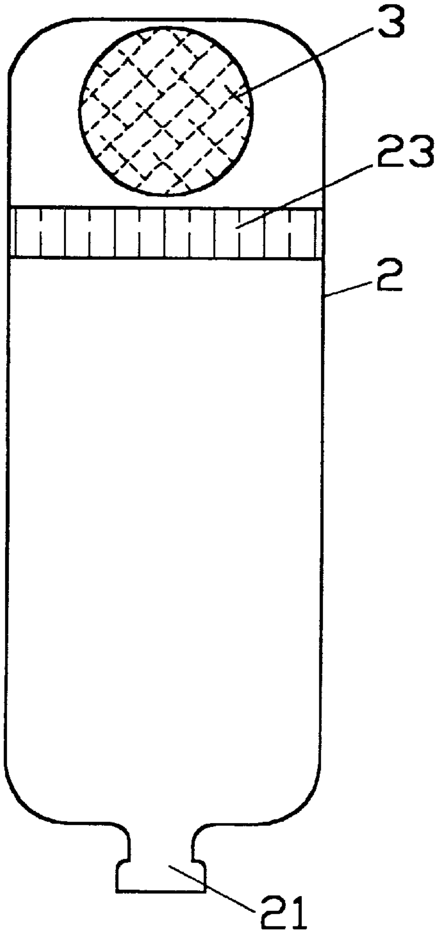
FIG. 3 is a plan view of the container for therapeutic use according to the first embodiment at a stage in the course of its production.
Figure 4:
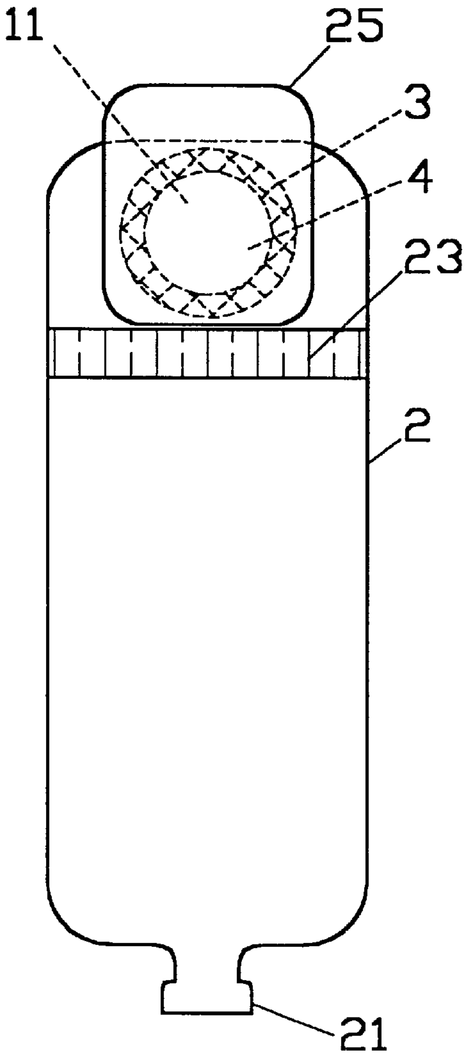
FIG. 4 is a plan view of the container for therapeutic use according to the first embodiment at another stage in the course of its production.

Reference is first had to FIG. 3. A main body of the container 1 is formed from a co-extruded parison by blow forming, and the narrow seal portion 23 and the welded region 3 are formed in the bag portion 2. As sealing conditions, the welding is conducted around 130° C. so that the narrow seal portion 23 and the welded region 3 are formed as peelable seals. As is shown in FIG. 4, a round punch is pressed against the welded region so that the openings 4A,4B are formed in the two walls of the bag portion, respectively (see FIG. 2). The opening 4A is used as the attachment hole 4. Over the attachment hole 4, an asepsis-retaining sheet 25 is peelably attached by thermal welding, and on a side opposite to the asepsis-retaining sheet 25, the cover member 11 is fixed by thermal welding and sealing. These thermal welding and sealing are conducted at 130° C. so that the peelability of the welded region 3 is not impaired. The interior of the container 1 is washed and the dried. After the dissolving solution 9 is caused to flow through a germ-proof filter, the dissolving solution 9 is filled in the bag portion 2 through the discharge port 21. After the filling, the discharge port 21 is closed by a rubber stopper.

Next, the container 1 is subjected to autoclave sterilization treatment at 100° C., whereby the dissolving solution 9 is autoclave-sterilized and, at the same time, the container 1 is wholly brought into a sterilized state.

On the other hand, the medicament 6 is lyophilized in the holder 5 so that the medicament 6 is aseptically stored in the holder 5. The container 1 and the holder 5 are placed in an aseptic operating chamber, in which the asepsis-retaining sheet 25 is peeled off from the container 1 and the holder 5 is hermetically attached over the attachment hole 4 of the container 1 by way of the flange portion 5A. Next, the upper part of the container 1 and the desiccant 8 are held between the folded two parts of the moisture-barrier sheet 7, the sheet 7 and the outer surfaces of the two walls of the bag-portion 2 are thermally welded and sealed and at the same time, the folded two parts of the sheet 7 are thermally welded and sealed together at side peripheral edges and upper portions thereof. Further, the sheet 7 and the outer surface of the flange portion 5A of the holder 5 are thermally welded and sealed together so that the desiccant 8 is completely sealed inside the sheet 7. A hole is formed through the upper portions of the sheet 7 to form the hang-up hole 24, whereby the container 1 for therapeutic use is obtained.

In the container 1 for therapeutic use constructed as described above, the attachment hole 4 can be easily formed in the container 1 upon its production. Despite the formation of the attachment hole 4, the interior of the container 1 can be early maintained free of germs by the asepsis-retaining sheet 25. Further, the holder 5 with the medicament 6 held therein can be easily and aseptically attached to the attachment hole 4.

During storage, moisture permeates into the holder 5 with the medicament 6 stored therein although the amount of the permeating moisture is extremely small. The interior of the holder 5 begins to be brought into equilibrium with the water vapor pressure in the surrounding atmosphere. However, the desiccant 8 inside the sheet 7 promptly absorb the moisture in the holder 5 through the cover member 11. The rate of permeation of moisture from the surrounding atmosphere is governed by the moisture permeability of the wall of the holder 5, whereas the rate of absorption of moisture in the desiccant 8 is determined by the moisture permeability of the cover member 11. As there is a difference as much as close to 50 times between their permeabilities, it is theoretically possible to lower the water vapor pressure in the holder 5 to about 1/50 of the water vapor pressure in the surrounding atmosphere.

Setting of the moisture permeability ratio of the wall of the holder 5 to the cover member 11 in the bag portion 2 within the above range makes it possible to sufficiently dry the interior of the holder 5 and hence to inhibit absorption of moisture in the medicament 6.

Owing to the moisture barrier property of the sheet 7, the desiccant 8 absorbs practically no moisture from the surrounding atmosphere directly through the sheet 7. Only a small portion of moisture in the surrounding atmosphere, said small portion having had permeated through the wall of the holder 5 and entered the holder 5, is to be absorbed in the desiccant 8. Even if the container 1 for therapeutic use is stored for a long time, the desiccant 8 does not absorb much moisture and can hence retain its function over an extended time.

Upon use, it is necessary to peel off the welded, narrow seal portion 23 and the welded region 3 by pressing the bag portion 2 in its entirety from the outside. As a result, the medicament 6 is aseptically dissolved in the dissolving solution 9, thereby making it possible to perform installation through the discharge port 21.

In the above-described embodiment, the welded, narrow seal portion 23 was provided so that the dissolving solution 9 was isolated as much as possible from the medicament 6 in the holder 5 to assure safety. It is however to be noted that the provision of the welded, narrow seal portion 23 is not absolutely needed.

In the above-described embodiment, the sparingly moisture-pervious, cyclic olefin resin was used as the material of the holder 5. As an alternative, a transparent, sparing moisture-pervious film provided with a functional resin layer, on which silica has been deposited, or a like film may be used.

In the above-described embodiment, the lyophilized medicament 6 was used as a medicament. However, the medicament is not limited to such a lyophilized medicament, but can be a protein which has been obtained by extraction and drying instead of lyophilization and which is susceptible to a change in property.

In the above-described embodiment, the attachment hole 4 was provided subsequent to the formation of the welded region 3. As an alternative, the attachment hole 4 may be formed in advance and the welded region 3 may then be arranged in the form of a ring around the attachment hole 4.

Second Embodiment

A container 31 for therapeutic use according to the second embodiment of the present invention will next be described with reference to FIG. 5 to FIG. 10.

As is illustrated in FIG. 5 to FIG. 10, the container 31 for therapeutic use is formed of a main body made of a flexible resin. Either a part or the entire part of a bag portion 32 of the main body is formed in a flat shape. Mutually-opposing two walls of the bag portion 32 are thermally and peelably welded together at inner surfaces thereof, whereby a welded region 33 is formed. At the welded region 33, a round through-hole 34 is formed. An opening defined bar the through-hole 34 in one of the walls of the bag portion 32 is used as an attachment hole 34A. An opening 34B defined by the through-hole 34 in the other wall of the bag portion 32 is hermetically covered by a cover sheet 41 the moisture permeability of which is 4.00 g/m$^2$·day or higher (as measured at 40° C. and 0–90% R.H. difference), whereby the cover sheet 41 serves as the other wall of the bag portion 32 at the position corresponding to the attachment hole 34A. The cover sheet 41 is formed of a silicone rubber sheet.

A holder 35 is thermally welded in an air- and liquid-tight fashion on an outer surface of the other wall of the bag portion 32 at an outer edge portion of the attachment hole 34A. An antibiotic 101, which tends to absorb moisture and to undergo a change in property or color, is hermetically accommodated within the holder 35. Extending over the cover sheet 41, a moisture-barrier cup 37 is fixed on an outer surface of the other wall via a ring-shaped fixing member 42. A desiccant 38 is placed within the cup 37.

Describing in further detail the container 31 for therapeutic use according to the second embodiment, each wall of the bag portion 32 of the container 31 for therapeutic use is formed of an inflation-formed sheet of 200 μm in thickness. In its flattened form, the bag portion 32 is 150 mm in length and 80 mm in width. The capacity of the bag portion 32 is 160 ml. Each wall of the bag portion 2 is formed of two layers, that is, an outer layer and an inner layer. The cuter layer is 150 μm in thickness and is made of linear low-density polyethylene (density: 0.935 g/cm$^3$, MI: 2, melting point: 121° C.), while the inner layer is 50 μm in thickness and is made of a 2:1 resin blend of linear low-density polyethylene (density: 0.935 g/cm$^3$, melting point: 121° C.) and polypropylene (density: 0.900 g/cm$^3$, MI: 0.7, melting point: 165° C.). The moisture permeability of each wall of the bag portion 32 is 3.0 g/m$^2$·day as measured at 40° C.

The bag portion 32 is provided with a discharge port 26, which is hermetically closed by a rubber stopper. A dissolving solution 99 is stored inside the bag portion 32. The dissolving solution 99 has been subjected along with the container 31 to autoclave sterilization treatment.

The welded region 33 has been formed to have such weld strength as it is peeled off when the internal pressure of the bag portion 32 is raised to about 0.2 Kgf/cm$^2$.

Figure 7:
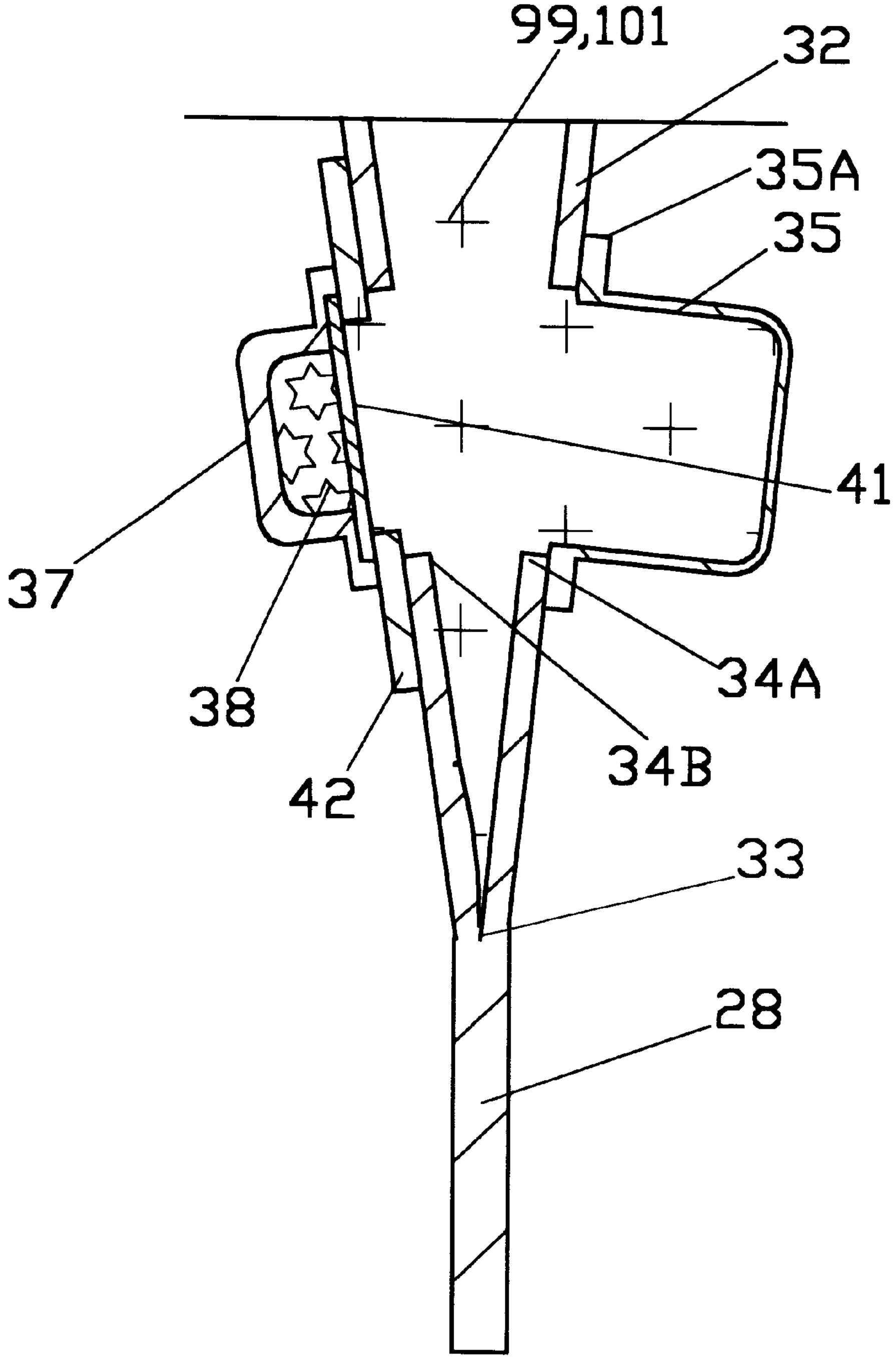
FIG. 7 is a fragmentary side cross-sectional view of the container for therapeutic use according to the second embodiment during use.

The cover sheet 41 is formed of a silicone rubber sheet, which is attached via the ring-shaped fixing member 42 to the other wall at a peripheral edge portion of the opening 34B as shown in FIG. 7. A peripheral edge portion of the silicone rubber sheet is held between the ring-shaped fixing member 42 and the cup 37, whereby the desiccant 38 is hermetically arranged within the cup 37.

The silicone rubber sheet is in the form of a disk having an outer diameter of 45.1 mm. Its thickness is 500 pm, and its permeability [P2] is 140 g/m$^2$·day as measured at 40° C. and 0–90% R.H. difference. Further, its effective area [A2] is 15 cm$^2$. The term "effective area" as used herein means the area of a portion of the silicone rubber sheet other than its outer peripheral portion which is held underneath a flange portion of the cup 37 and does not take part in allowing moisture to permeate through the silicone rubber sheet from the interior of the holder 35 into the interior of the cup 37.

The ring-shaped fixing member 42 is made of high-density polyethylene resin and is thermally welded in an air-and liquid-tight fashion on the outer surface of the other wall of the bag portion 32.

The cup 37 has been formed by vacuum-forming a multi-layered sheet in which an aluminum foil is laminated, and has been thermally welded in an air- and liquid-tight fashion on the outer surface of the ring-shaped fixing member 42. The moisture permeability of the wall of the cup 37 is 0.05 g/m$^2$·day or lower as measured at 40° C. and 0–90% R.H. difference. The desiccant 38 consists of 5 g of a molecular sieve.

The holder 35 has been formed in the shape of a cup by using a transparent thermoplastic resin. The holder 35 is provided with a flange portion 35A around an opening thereof. The flange portion 35A and a peripheral edge portion of the attachment hole 34A have been thermally welded and sealed together in an air- and liquid-tight fashion.

The holder 35 has been formed from a resin sheet composed of an outer layer, a middle layer and an inner layer. The outer layer is 100 μm in thickness and is made of low-density polyethylene. The middle layer is 3,000 μm in thickness and is made of a cyclic polyolefin resin. The inner layer is 100 μm in thickness and is made of linear low-density polyethylene. The moisture permeability [P1] of the wall of the holder 35 is 0.05 $g/m^2 \cdot 24$ hr as measured at 40° C. and 0–90% R.H. difference. The wall area [A1] of the holder 35 is 45 $cm^2$.

A description will be made in brief about a process for the production of the container 1 for therapeutic use according to the second embodiment.

Figure 5:
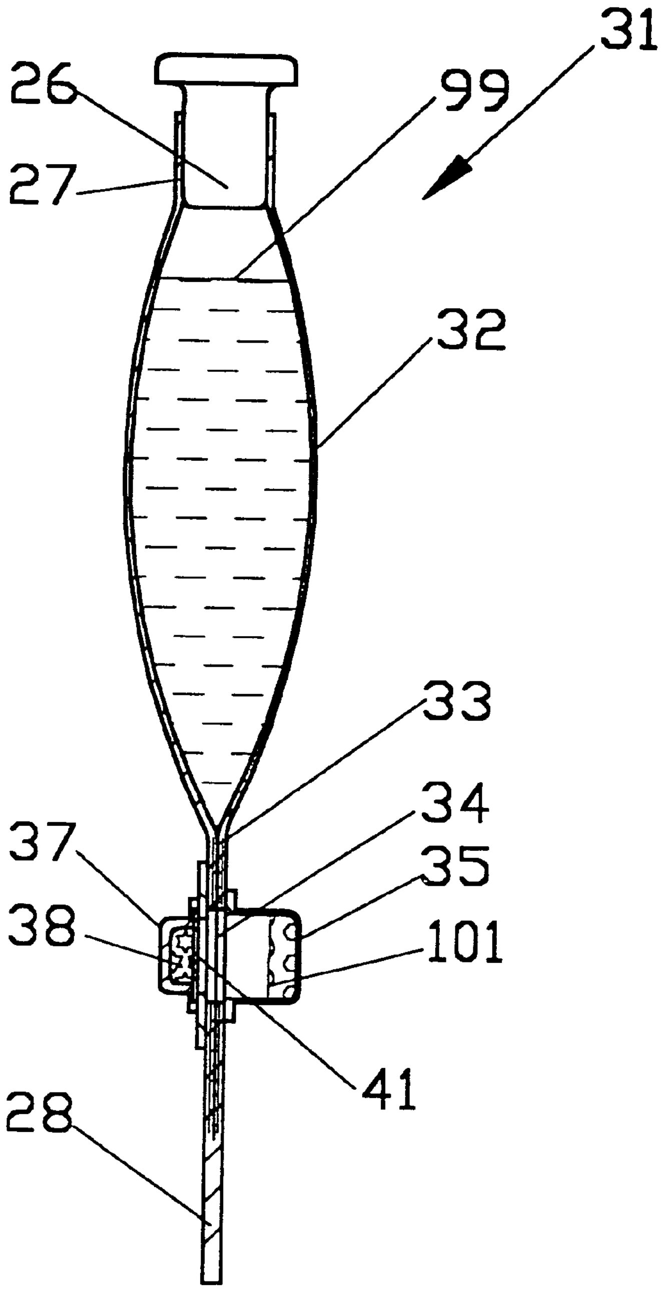
FIG. 5 is a cross-sectional view of a container for therapeutic use according to a second embodiment of the present invention.
Figure 6:
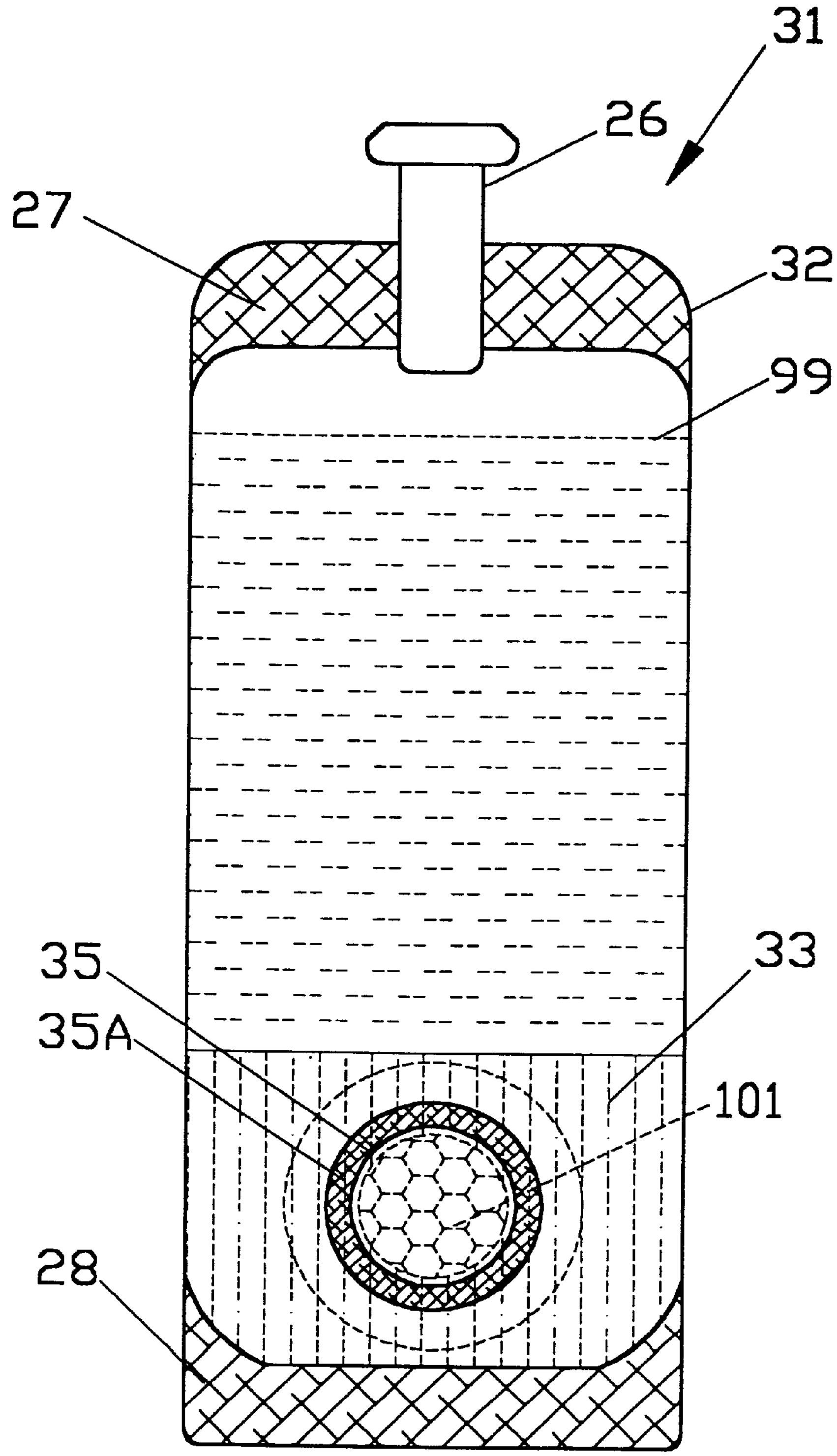
FIG. 6 is a plan view of the container for therapeutic use according to the second embodiment.

As is illustrated in FIG. 5 and FIG. 6, the above-described inflation sheets are cut in predetermined lengths. Cut end portions 27,28 are hermetically sealed to form the bag portion 32 as the container main body. Upon performing the hermetic sealing, the discharge port 26 is attached to the cut end portion 27. The hermetic sealing is performed at 170° C., whereby the end portions 27,28 are formed into welded, unpeelable seals.

At a part of the bag portion 32, the walls of the bag portion 32 are thermally welded together at the inner surfaces thereof to form the welded peelable region 33. The thermal welding of the welded region 33 is conducted at 140° C. The through-hole 34 is then formed by a punch through the welded region 33.

The silicone rubber sheet as the cover sheet 41 is applied onto the ring-shaped fixing member 42. The ring-shaped fixing member 42 is then fixed on the outer surface of the other wall in the welded region 33 by thermal welding and sealing, whereby the opening 34B defined by the through-hole 34 in the other wall is covered by the silicone rubber sheet. The thermal welding and sealing is conducted at 130° C. Further, an asepsis-retaining sheet is peelably applied over the attachment hole 34A on the opposite side, so that the attachment hole 34A is prevented from being exposed to the contaminated surrounding atmosphere. The ring-shaped attachment member 42 and the asepsis-retaining sheet are thermally welded on the outer surfaces of the walls of the bag portion 32 at such temperatures as the welded region 33 formed by thermally welding together the inner surfaces of the walls of the bag portion 32 does not lose its peelability. Incidentally, the asepsis-retaining sheet may desirably be provided with an inner layer made of a blend resin of polyethylene and polypropylene and also with a middle layer carrying a deposited aluminum layer thereon.

Then, the dissolving solution 99 is filled in the bag portion 32 through the discharge port 26, and the discharge port 26 is hermetically sealed by a rubber stopper. After the hermetic sealing, the container 31 is subjected to autoclave sterilization treatment at 110° C.

Figure 8:
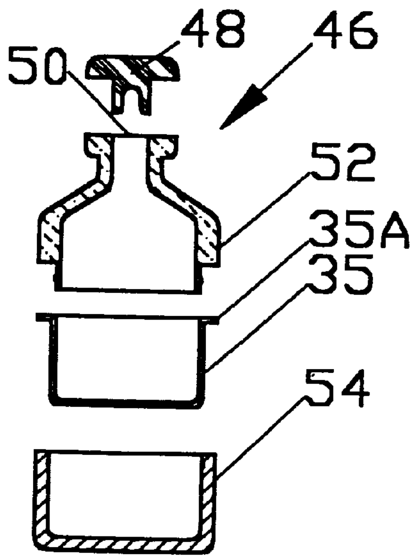
FIG. 8 is an exploded cross-section view of a vial provided with a medicament holder of the container for therapeutic use according to the second embodiment.
Figure 9:
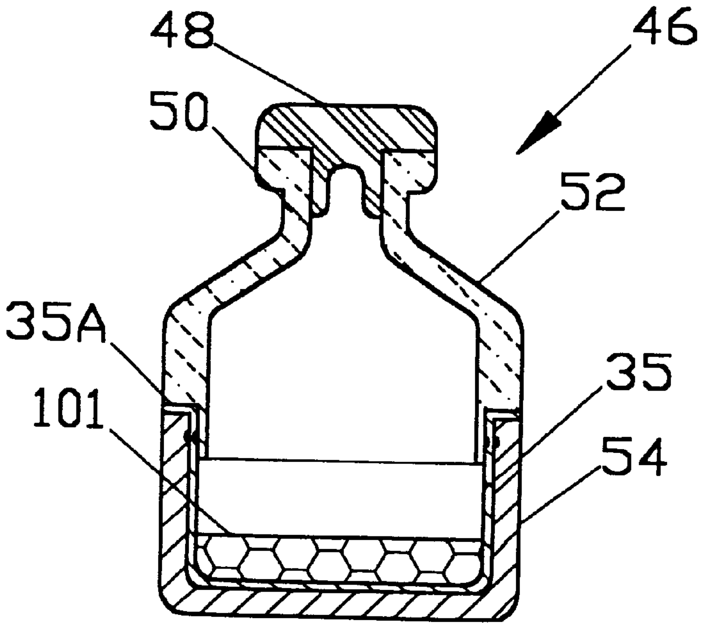
FIG. 9 is a cross-sectional view of the vial provided with the medicament holder of the container for therapeutic use according to the second embodiment.
Figure 10:
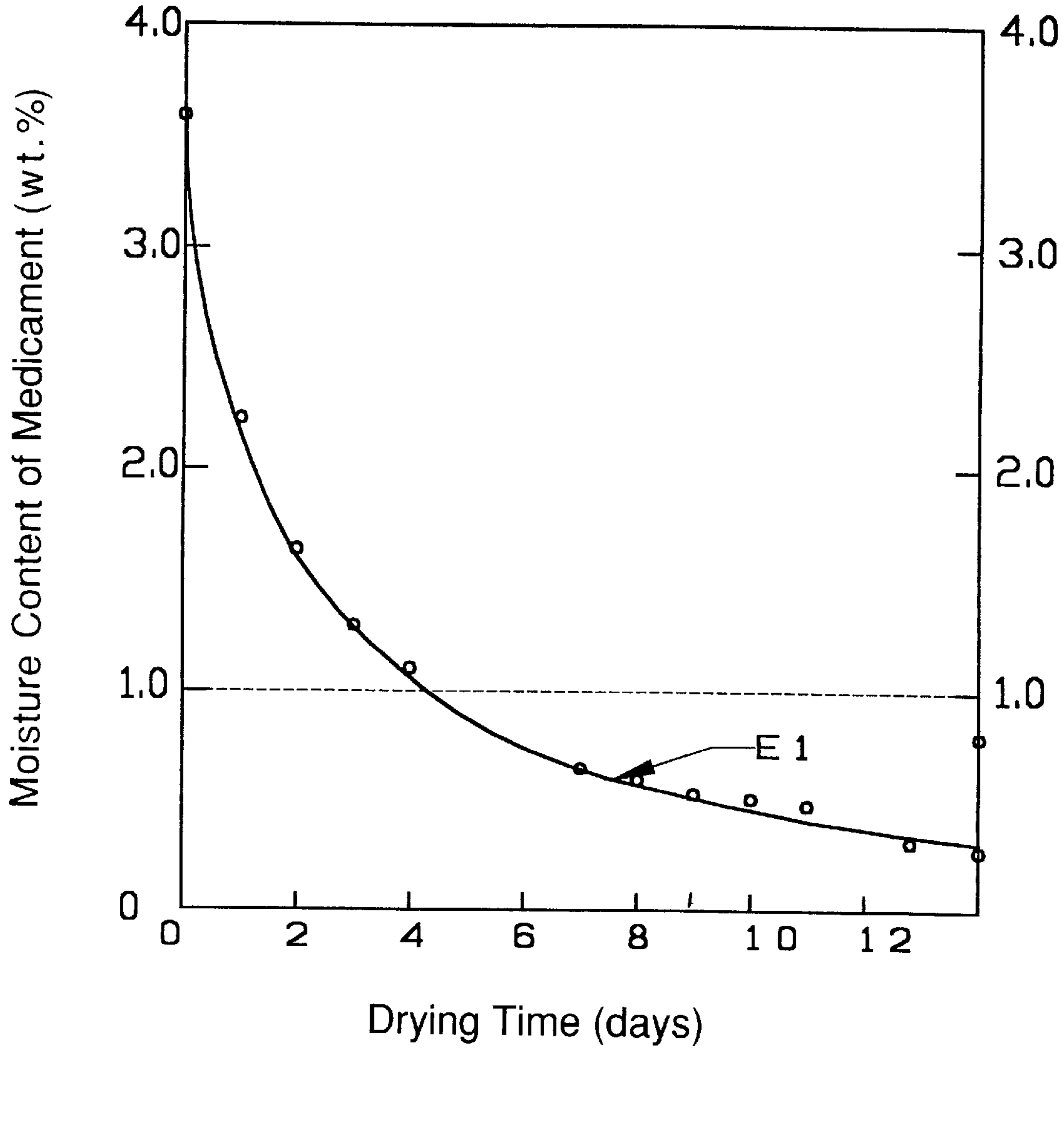
FIG. 10 is a diagrammatic representation of the water content of a medicament in the holder as a function of its drying time in the vial provided with the medicament holder of the container for therapeutic use according to the second embodiment.

On the other hand, the cup-shaped medicament holder 35 is formed by vacuum forming and, as is depicted in FIG. 8 and FIG. 9, is arranged in a vial 46. The vial 46 is composed of an upper half 52 provided with an opening 50 and a lower half 54 in which the medicament holder 35 is arranged. A semi-closable rubber stopper 48 is fitted in the opening 50.

The medicament holder 35 is fitted in the lower half 54, and the upper half 52 and the lower half 54 are combined together. Through the opening 50 of the upper half 52, a medicament solution to be lyophilized is filled through a germ-proof filter. Subsequent to the filling, the rubber stopper 48 is fitted in the opening 50 to achieve a semi-closed state. The vial 46 with the medicament holder 35 fitted therein is then placed in a lyophilizing vessel. Lyophilization of the medicament solution is completed to form the antibiotic 101 in the holder 35. The rubber stopper 48 is then completely fitted in the opening 50. The vial 46 is then placed in a clean room the environment of which is maintained germ-free.

The container 31, which has been sterilized as described above, is placed in the clean room, and the asepsis-retaining sheet (not shown) is peeled off from the attachment hole 34A of the bag portion 32. Further, the upper half 52 of the vial 46, in which the antibiotic 101 obtained by the lyophilization is contained, is detached from the lower half 54. The medicament holder 25 is then aseptically connected to the attachment hole 34A. This connection is conducted by thermally welding and sealing the flange 35A onto the outer surface of the one wall of the bag portion 32 at the peripheral edge portion of the attachment hole 34A. This thermal welding and sealing is conducted at 130° C. It should also be conducted by paying attention so that the peelability of the welded region 33 is not be lost.

The desiccant 38 is next filled in the cup 37 and, while holding the peripheral edge portion of the silicone rubber sheet 41 between the ring-shaped fixing member 42 and the flange portion of the cup 37, the flange portion of the cup 37 is fixed onto the ring-shaped fixing member 42 by thermal welding and sealing.

The container 31 for therapeutic use constructed as described above brings about the following merits in the course of its production. First, it is possible to form the welded region 33 readily and also to form the through-hole 34 easily. The medicament holder 35 can be easily attached to the one wall of the flat bag portion 32 by thermal welding or the like. Owing to the application of the asepsis-retaining sheet over the attachment hole 34A before autoclave sterilization, the interior of the bag portion 32 can be maintained germ-free until shortly before the connection of the medicament holder 35. It is therefore possible to perform safely and easily the aseptic connection of the medicament holder 35 with the bag portion 32 as the main body of the container 31.

The container 31 for therapeutic use constructed as described above shows the following advantages during its storage. The antibiotic 101 is protected from a change in property by moisture, and the drying function of the desiccant 38 remains for an extended time.

As the medicament holder 35 is made of the resin, moisture penetrates from the surrounding atmosphere into the holder 35 although the amount of the moisture is not much. Even the moisture so penetrated is allowed to promptly pass through the cover sheet 41 and is absorbed in the desiccant 38 inside the cup 37. The interior of the holder 35 is therefore always kept dry, and the antibiotic 101 is protected from the potential problem of a change in property.

Namely, by introducing [A1]=45[A2]/15 and [P1]=0.05 [P2]/140 into [W2]=[A1]·[P1]·[W1]/([A1]·[P1]+[A2]·[P2]), [W2]=$1.06\times10^{-3}$[W1] is obtained. If the water vapor pressure [W1] in the surrounding atmosphere is 21.4 mmHg, the water vapor pressure [W2] in the holder 35 can then be calculated to be $2.29\times10^{-2}$ mmHg.

A severe test was actually conducted, in which the container 31 was left over for 1 month in an atmosphere of 40° C. and 90% R.H. The potency of the antibiotic 101, which was employed as an example of the medicament, was not lowered.

Using two samples of the container 31 for therapeutic use, the following experiment was conducted.

As a medicament, "Pentcillin" (trade mark; product of Toyama Chemical Co., Ltd.) was obtained in a lyophilized form. The medicament was left over in a place of 40% R.H.

for a predetermined time, so that it was allowed to absorb moisture. About 2 grams of the moisture-absorbed medicament were weighed. precisely and then placed within the holder 35. The holder 35 was then thermally welded to the outer surface of the one wall of the bag portion 32 of the container 31 at the outer edge portion of the attachment hole 34A, so that the holder 35 was connected to the bag portion 32. The above procedures were repeated to produce two container samples (E1,E2) of the second embodiment in total. They were placed in a room controlled at 60° C. Decreases in the weight and moisture content of the "Pentcillin" in the holder 35 were determined everyday over 2 weeks. In addition, a standard container (SD) was also produced to determine the content of moisture absorbed in "Pentcillin" when it was left over as the initial procedure. The standard container had a construction so that a hole was formed through a part of the cover sheet to permit free movement of moisture between the interior of the holder 35 and the interior of the cup 37, the latter interior containing the desiccant 38 therein. The amount of moisture eliminated from the "Pentcillin" in the standard container was recorded as an initial moisture content. The results are shown in Table 1 and Table 2. Incidentally, from the results shown in Table 1, an SD value can be calculated as follow: SD=(2.0044−1.9324)×100/2.0044=3.59 (wt. %). From these results, Table 2 was prepared. Further, a relationship between the drying time (days) and the moisture content (wt. %) of the "Pentcillin" stored in the container sample E1 is shown FIG. 10.

TABLE 1

Time of storage of each container at 60° C. and the weight (g) of "Pentcillin" stored in the container

| | Container | | |
|---|---|---|---|
| | Containers of second embodiment | | Standard container |
| Time (days) | Sample E1 | Sample E2 | SD |
| 0 | 2.0085* | 2.0101* | 2.0044* |
| 1 | 1.9810 | 1.9845 | 1.9577 |
| 2 | 1.9693 | 1.9717 | 1.9486 |
| 3 | 1.9627 | 1.9649 | 1.9439 |
| 4 | 1.9584 | 1.9608 | 1.9413 |
| 7 | 1.9493 | 1.9534 | 1.9368 |
| 8 | 1.9483 | 1.9520 | 1.9359 |
| 9 | 1.9471 | 1.9506 | 1.9354 |
| 10 | 1.9468 | 1.9500 | 1.9362 |
| 11 | 1.9459 | 1.9491 | 1.9347 |
| 13 | 1.9426 | 1.9454 | 1.9326 |
| 14 | 1.9421 | 1.9450 | 1.9324 |

*initial values

TABLE 2

Moisture content (wt. %) of "Pentcillin"

| | Container Containers of second embodiment | |
|---|---|---|
| Time (days) | Sample E1 | Sample E2 |
| 0 | 3.59* | 3.59* |
| 1 | 2.22 | 2.32 |
| 2 | 1.64 | 1.68 |
| 3 | 1.31 | 1.34 |
| 4 | 1.10 | 1.14 |
| 7 | 0.64 | 0.77 |
| 8 | 0.59 | 0.70 |

TABLE 2-continued

Moisture content (wt. %) of "Pentcillin"

| | Container Containers of second embodiment | |
|---|---|---|
| Time (days) | Sample E1 | Sample E2 |
| 9 | 0.53 | 0.63 |
| 10 | 0.52 | 0.60 |
| 11 | 0.48 | 0.56 |
| 13 | 0.31 | 0.37 |
| 14 | 0.28 | 0.35 |

*initial values

It is understood that the moisture content of the "Pentcillin" stored in the container 31 for therapeutic use according to the second embodiment is lowered to about 1 wt. % or less in 4 days. From the above results, it is desired to form the other wall of the bag portion 32 at the position corresponding to the attachment hole 34A, namely, the cover sheet 41 with a material having a moisture permeability [P] of 4.0 $g/m^2$·day or higher as measured at 40° C. and 0–90% R.H. difference, especially of 20.0 $g/m^2$·day or higher as measured at 40° C. and 0–90% R.H. difference. It is also desired to remove moisture from the medicament in the holder at an early stage. Especially, to promote the release of moisture from the medicament and also the permeation of moisture through the cover sheet, it is desired to place the container 31 for therapeutic use in a place the temperature of which is 40° C. or higher. This makes it possible to decrease the moisture content of the medicament in a short time. Owing to such a decrease in the moisture content, the properties of the medicament can be stably retained during the subsequent storage period of the container for therapeutic use. In general, a medicament has a potential problem that it tends to undergo a thermal change in property if the temperature exceeds 80° C. It is therefore desired to control the treatment temperature for the container for therapeutic use below 80° C. during drying.

In the container 31 for therapeutic use, the container main body is pressed from the outside upon use. As a result, the welded region 33 is peeled off as illustrated in FIG. 7. By this peeling-off, the interior of the medicament holder 35 and the interior of the bag portion 32 are communicated with each other, so that the antibiotic 101 as the lyophilized medicament is dissolved in the dissolving solution 99.

Figure 11:
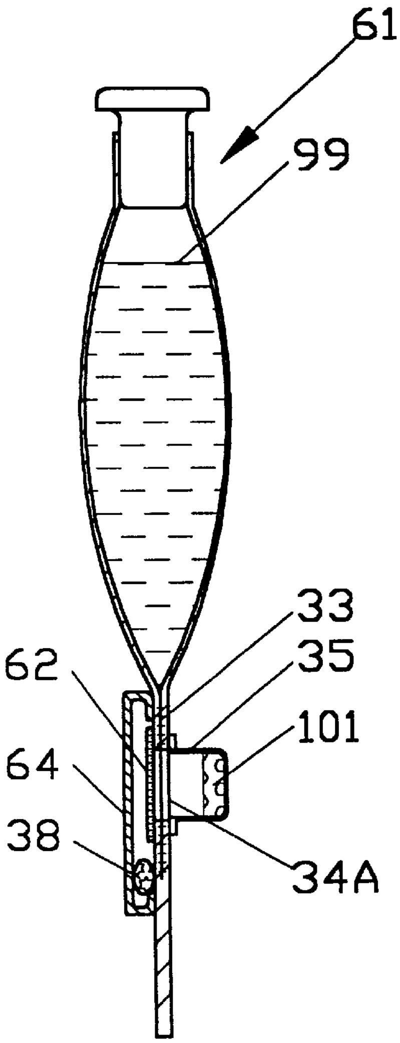
FIG. 11 is a cross-sectional view of a container as a modification of the container for therapeutic use according to the second embodiment.
Figure 12:
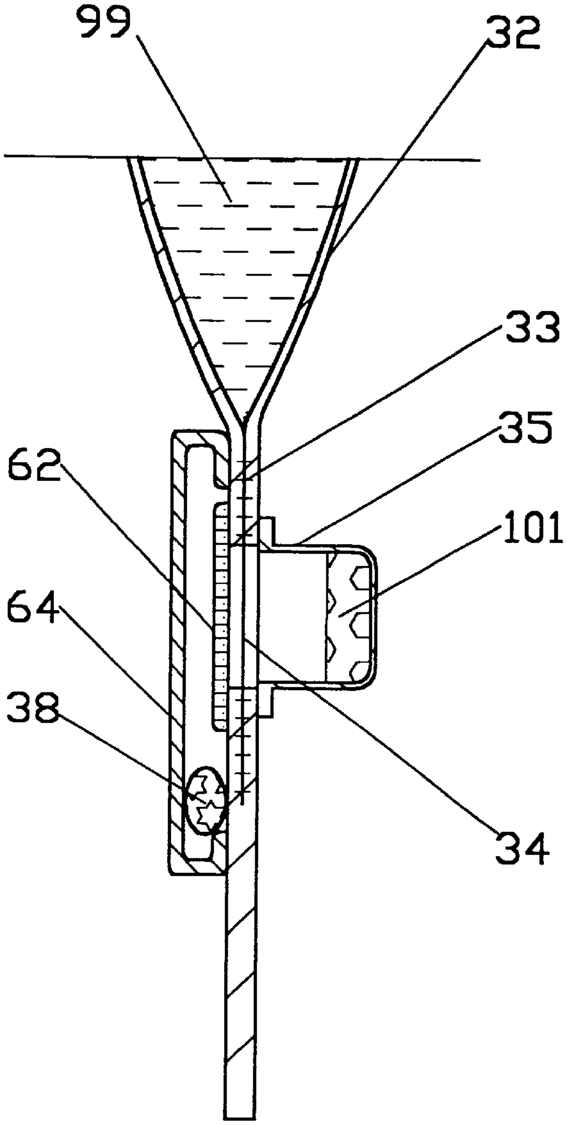
FIG. 12 is a fragmentary cross-sectional view of the container as the modification of the container for therapeutic use according to the second embodiment.

With reference to FIG. 11 and FIG. 12, a container 61 for therapeutic use will next be described. The container 61 for therapeutic use is a modification of the container 31 for therapeutic use according to the second embodiment. The container 61 for therapeutic use has substantially the same construction as the container 31 for therapeutic use according to the second embodiment. Therefore, upon describing the container 61 for therapeutic use, members and ingredients similar to the corresponding ones in the container 31 for therapeutic use are identified by like reference signs in FIG. 11 and FIG. 12, and their detailed description is omitted herein.

The container 61 for therapeutic use is different from the container 31 for therapeutic use in that as the cover member 62, a microporous film is used in place of the silicone rubber sheet. Further, the moisture-barrier member 64 is made of a laminated sheet, which includes an aluminum foil, instead of the cup 37.

The cover member 62 is made of a sheet which has been formed by flash-spinning high-density polyethylene and thermally bonding the resultant fibers with each other. It has a basis weight of 75.0 $g/m^2$, a thickness of 200 $\mu$m, a Gurley air permeability of 21 seconds/100 ml, a particle blocking rate of 99% or higher at a particle diameter of from 0.5 to 0.7 $\mu$m, a moisture permeability of 4,000 $g/m^2$·day (as measured at 40° C.), and a water pressure resistance of 1,400 $mmH_2O$. Therefore, the material of the cover member 62 is substantially pervious to moisture and is thermally weldable and sealable on the outer surface of the other wall of the bag portion 32.

The moisture-barrier member 64 is made of a transparent, multi-layered resin film, the inner and outer layers of which are formed of sealing layers made of low-density polyethylene and the middle layer of which is a polyethylene terephthalate layer with silica deposited thereon. Accordingly, the moisture permeability of the wall of the member 64 is 0.05 $g/m^2$·day as measured at 40° C. and 0–90% R.H. difference.

The container 61 for therapeutic use constructed as described above can be produced easily and safely like the container 31 for therapeutic use.

In the container 61 for therapeutic use constructed as described above, moisture is allowed to pass practically freely through the wall of the cover member 62. The space, in which the desiccant 38 is stored, and the interior of the holder 35 therefore do not differ in dryness. Accordingly, the antibiotic is kept dry by the desiccant 38.

In the container 61 for therapeutic use constructed as described above, the bag portion 32 is pressed from the outside upon use. As a result, the welded region 33 is peeled off. By this peeling-off, the interior of the medicament holder 35 and the interior of the bag portion 32 are communicated with each other, so that the antibiotic 101 is dissolved in the dissolving solution 99. Here, the dissolving solution 99 is brought into contact with the wall of the cover member 62. As this wall has waterproofness as described above, there is no potential problem of leakage of the dissolving solution 99 even when the bag portion 32 is pressed rather strongly.

What is claimed is:

1. A container for therapeutic use, comprising a main body made of a flexible resin, comprising:

a bag portion having an interior or accommodating a medium to be mixed with a medicament prior to use;

a flat portion including a welded region where mutually-opposing walls are peelably welded together, one of the mutually-opposing walls having an attachment hole for communicating with the medicament, said attachment hole being surrounded by the welded region, the other of the mutually-opposing walls having an interposing wall where said attachment hole is located, said flat portion having two sides facing away from each other, one of which is a medicament side formed by said one of the mutually-opposing walls, the other of which is a desiccant side formed by said other of the mutually-opposing walls;

a holder having an interior where the medicament is pre-loaded, said medicament being prone to a change in property or color upon absorption of moisture, said holder pre-loaded with the medicament being hermetically attached to the flat portion to accommodate the medicament on the medicament side over said attachment hole to seal said medicament in said holder, wherein the interior of the holder communicates with the interior of the bag portion through the attachment hole by peeling at least a part of the welded region when mixing the medium and the medicament; and a moisture-barrier member having an interior accommodating a desiccant placed therein, said moisture-barrier member being hermetically attached to the flat portion to accommodate the desiccant on the desiccant side over said interposing wall, said interior of the moisture-barrier member being isolated from the interior of the holder by the interposing wall, said holder being non-enclosed by the moisture-barrier member, wherein moisture in the interior of the holder is controlled by the desiccant through the interposing wall.

2. The container according to claim 1, wherein said holder is formed with a wall having a moisture permeability within a range not higher than 1/10 of a permeability of the interposing wall of said position.

3. The container according to claim 2, wherein the permeability of said wall of said holder is not higher than 1.0 $g/m^2$·day as measure at 40° C. and 0–90% relative humidity difference.

4. The container according to claim 3, wherein said wall of said holder is provided with a cyclic olefin resin layer.

5. The container according to claim 2, wherein a through-hole is formed through the other of the mutually-opposing walls of said bag portion in said welded region, and the interposing wall is a cover member hermetically attached to the other of the mutually-opposing walls, said cover member having a water vapor permeability of at least 4.00 $g/m^2$·day as measured at 40° C. and 0–90% relative humidity difference.

6. The container according to claim 5, wherein said cover member is made of a silicone rubber sheet.

7. The container according to claim 5, wherein said cover member is made of a microporous film of moisture free permeability, which has a particle blocking rate of at least 99% for particles having diameters of at least 0.8 $\mu$m and a water impermeability of at least 500 $mmH_2O$ in terms of water pressure resistance.

8. The container according to claim 2, wherein said medicament is a lyophylized product subjected to lyophilization within said holder.

9. The container according to claim 1, wherein said holder is formed with a wall having a moisture permeability within a range of from 1/10 to 1/1000 of a permeability of the interposing wall of said flat portion.

10. The container according to claim 1, wherein said moisture-barrier member is pre-loaded with the desiccant before being attached to the flat portion.

11. The container according to claim 1, wherein said welded region is annularly formed around said attachment hole.

12. The container according to claim 1, wherein said other of the mutually-opposing walls has a through-hole over the attachment hole of said one of the mutually-opposing walls, and the interposing wall is a cover member hermetically attached to the other of the mutually-opposing walls over the through-hole.

13. The container according to claim 12, wherein said cover member has higher moisture permeability than the mutually-opposing walls.

14. A method for the production of a container for therapeutic use as defined in claim 5, which comprises:

thermally and peelably welding mutually-opposing walls of a bag portion of a flexible container together at inner surfaces thereof to form a welded region at at least a part of said bag portion;

forming a through-hole in both the walls of said bag portion in said welded region;

attaching a holder with a medicament placed therein, said medicament being prone to a change in property or color upon absorption of moisture, onto one of said walls so that an opening formed as an attachment hole in the one wall by said through-hole is covered by said holder;

covering an opening, which has been formed in the other wall by said through-hole, by a cover member having a moisture permeability of at least 4.00 $g/m^2 \cdot day$ as measured at 40° C. and 0–90% relative humidity difference; and attaching a moisture-barrier member, which contains a desiccant placed therein, onto the other wall of said bag portion on a side opposite to said holder so that said cover member is hermetically covered by said moisture-barrier member.

* * * * *

UNITED STATES PATENT AND TRADEMARK OFFICE

CERTIFICATE OF CORRECTION

PATENT NO. : 6,162,205
DATED : December 19, 2000
INVENTOR(S) : Hiroyuki Shichi, Takao Yoshida, Tatsuo Suzuki and Keinosuke Isono It is certified that error appears in the above-identified patent and that said Letters Patent is hereby corrected as shown below:

Title page,
Item [73], Assignee, please correct "Mateial Engineering Technology Laboratory, Incorporated" to -- Material Engineering Technology Laboratory, Incorporated --.

Signed and Sealed this

Fifth Day of March, 2002

*Attest:*

JAMES E. ROGAN

*Attesting Officer* *Director of the United States Patent and Trademark Office*